US00RE37796E

(19) United States
(12) Reissued Patent
Henley

(10) Patent Number: US RE37,796 E
(45) Date of Reissued Patent: Jul. 23, 2002

(54) METHODS FOR IONTOPHORETIC DELIVERY OF ANTIVIRAL AGENTS

(75) Inventor: Julian L. Henley, Guilford, CT (US)

(73) Assignee: Biophoretic Therapeutic Systems, LLC, Framingham, MA (US)

(21) Appl. No.: 09/654,583

(22) Filed: Sep. 1, 2000

Related U.S. Patent Documents

Reissue of:
(64) Patent No.: 5,908,401
Issued: Jun. 1, 1999
Appl. No.: 08/991,827
Filed: Dec. 16, 1997

(51) Int. Cl.[7] ..... A61N 1/30; A61M 31/00
(52) U.S. Cl. ..... 604/20; 604/501
(58) Field of Search ..... 601/2, 17; 607/154, 607/145, 3; 604/19, 20, 22, 49, 66, 289, 290, 890.1, 500, 501

(56) References Cited

U.S. PATENT DOCUMENTS

| | | | |
|---|---|---|---|
| 279,524 | A | 6/1883 | Beaty |
| 484,522 | A | 10/1892 | McBride |
| 600,290 | A | 3/1898 | Muir |
| 2,129,070 | A | 8/1938 | Wappler |
| 2,834,344 | A | 5/1958 | Kanai |
| 3,019,787 | A | 1/1962 | Simmons |
| 3,048,170 | A | 8/1962 | Lemos |
| 3,107,672 | A | 10/1963 | Hofmann |
| 3,163,166 | A | 12/1964 | Brant et al. |

(List continued on next page.)

FOREIGN PATENT DOCUMENTS

| | | | | |
|---|---|---|---|---|
| AT | 0232642 | | 3/1964 | ..... 604/20 |
| EP | 617979 | A1 | 10/1994 | |
| FR | 1445703 | | 6/1966 | ..... 604/20 |
| GB | 0299553 | | 11/1928 | ..... 604/20 |

OTHER PUBLICATIONS

"Iontophoretic Treatment of Oral Herpes," Henley et al.; Laryngoscope, vol. 94, No. 1, pp. 118–121, Jan. 1984.
"Iontophoretic Application of Idoxuridine for Recurrent Herpes Labialis: Report of Preliminary Chemical Trials," Gangarosa et al.; Meth. And Find. Exptl. Clin. Pharmacol. 1(2), pp. 105–109 (1979).
"Iontophoresis of Vidarabine Monophosphate for Herpes Orolabialis," Gangarosa et al.; The Journal of Infectious Diseases, vol. 154, No. 6, pp. 930–934, Dec. 1986.
"The Natural History of Recurrent Herpes Simplex Labialis," Spruance et al.; The New England Journal of Medicine, vol. 297, No. 2, pp. 69–75, Jul. 14, 1977.
"Infection with Herpes–Simplex Viruses 1 and 2," Nahmias et al.; The New England Journal of Medicine, pp. 667–674, Sep. 27, 1973.
"Anesthesia of the Human Tympanic Membrane by Iontophoresis of a Local Anesthetic," Comeau et al.; The Laryngoscope, 88:1978, pp. 277–285.

(List continued on next page.)

*Primary Examiner*—Sharon Kennedy
(74) *Attorney, Agent, or Firm*—Nixon & Vanderhye

(57) ABSTRACT

A portable iontophoresis apparatus for facilitating delivery of medication across the cutaneous membrane into adjacent underlying tissues and blood vessels. The apparatus employs a modular, detachable non-reusable medicament-containing applicator electrode which is adapted to attach to a base assembly. The apparatus is designed to be hand-held and includes a circumferential tactile electrode band on the base assembly which provides electrical connection between the skin of the user's hand and one pole of a bipolar power source housed within the base assembly. The opposing pole of the power source is connected to the applicator electrode. The user's body completes the electrical circuit between the applicator and tactile electrodes A method for using the device for the treatment of Herpes simplex infection and related viral infections which produce similar cutaneous lesions is presented. The apparatus, when used in accordance with the method described herein, demonstrated >90% treatment efficacy in clinical trials.

6 Claims, 2 Drawing Sheets

U.S. PATENT DOCUMENTS 3,298,368 A 1/1967 Charos
3,520,297 A 7/1970 Bechtold
3,645,260 A 2/1972 Cinotti et al.
3,716,054 A 2/1973 Porter et al.
3,831,598 A 8/1974 Tice
4,325,367 A 4/1982 Tapper
4,383,529 A 5/1983 Webster
4,474,570 A 10/1984 Ariura et al.
4,510,939 A 4/1985 Brenman et al.
4,665,921 A 5/1987 Teranishi et al.
4,689,039 A 8/1987 Masaki
4,702,732 A 10/1987 Powers et al.
4,747,819 A 5/1988 Phipps et al.
4,787,888 A 11/1988 Fox
4,838,273 A 6/1989 Cartmell
4,913,148 A 4/1990 Diethelm
4,919,648 A 4/1990 Sibalis
4,953,565 A 9/1990 Tachibana et al.
4,957,480 A 9/1990 Morenings
4,979,938 A 12/1990 Stephen et al.
4,997,418 A 3/1991 DeMartini
5,037,381 A 8/1991 Bock et al.
5,042,975 A 8/1991 Chien et al.
5,090,402 A 2/1992 Bazin et al.
5,133,352 A 7/1992 Lathrop et al.
5,160,316 A 11/1992 Henley
5,162,042 A 11/1992 Gyory et al.
5,169,384 A 12/1992 Bosniak et al.
5,203,768 A 4/1993 Haak et al.
5,250,022 A 10/1993 Chien et al.
5,279,543 A 1/1994 Glikfeld et al.
5,284,471 A 2/1994 Sage, Jr.
5,298,017 A 3/1994 Theeuwes et al.
5,312,326 A 5/1994 Myers et al.
5,314,502 A 5/1994 McNichols et al.
5,331,979 A 7/1994 Henley
5,354,321 A 10/1994 Berger
5,360,440 A 11/1994 Andersen
5,362,307 A 11/1994 Guy et al.
5,362,308 A 11/1994 Chien et al.
5,374,241 A 12/1994 Lloyd et al.
5,374,242 A 12/1994 Haak et al.
5,376,107 A 12/1994 Inagi et al.
5,391,195 A 2/1995 Van Groningen
5,395,310 A 3/1995 Untereker et al.
5,413,590 A 5/1995 Williamson
5,415,629 A 5/1995 Henley
5,421,816 A 6/1995 Lipkovker
5,441,936 A 8/1995 Houghten et al.
5,443,441 A 8/1995 De Claviere
5,458,569 A 10/1995 Kirk et al.
5,464,387 A 11/1995 Haak et al.
5,466,217 A 11/1995 Myers et al.
5,470,349 A 11/1995 Kleditsch et al.
5,494,679 A 2/1996 Sage, Jr. et al.
5,501,705 A 3/1996 Fakhri
5,514,167 A 5/1996 Smith et al.
5,558,632 A 9/1996 Lloyd et al.
5,562,607 A 10/1996 Gyory
5,589,563 A 12/1996 Ward et al.
5,603,693 A 2/1997 Frenket et al.
5,607,461 A 3/1997 Lathrop
5,607,691 A 3/1997 Hale et al.
5,618,275 A 4/1997 Bock
5,658,247 A 8/1997 Henley
5,667,487 A 9/1997 Henley
5,668,170 A 9/1997 Gyory
5,676,648 A 10/1997 Henley
5,688,233 A 11/1997 Hofmann et al.
5,697,896 A 12/1997 McNichols et al.
5,700,457 A 12/1997 Dixon
5,711,761 A 1/1998 Untereker et al.
5,713,846 A 2/1998 Bernhard et al.
5,722,397 A 3/1998 Eppstein
5,725,817 A 3/1998 Milder
5,733,255 A 3/1998 Dinh et al.
5,755,750 A 5/1998 Petruska et al.
5,788,666 A 8/1998 Atanasoska
5,795,321 A 8/1998 McArthur et al.
5,797,867 A 8/1998 Guerrara et al.
5,830,175 A 11/1998 Flower
5,840,057 A 11/1998 Alosi
5,846,217 A 12/1998 Beck et al.
5,879,323 A 3/1999 Henley
5,882,676 A 3/1999 Lee et al.
5,908,401 A 6/1999 Henley
5,919,155 A 7/1999 Lattin et al.
5,931,859 A 8/1999 Burke
5,935,598 A 8/1999 Sage et al.
5,961,482 A 10/1999 Chien et al.
5,961,483 A 10/1999 Sage et al.
5,968,005 A 10/1999 Tu
5,968,006 A 10/1999 Hofmann
5,983,130 A 11/1999 Phipps et al.
6,004,309 A 12/1999 Phipps
6,004,547 A 12/1999 Rowe et al.
6,006,130 A 12/1999 Higo et al.
6,018,679 A 1/2000 Dinh et al.
6,023,639 A 2/2000 Hakky et al.
6,032,073 A 2/2000 Effenhauser
6,038,485 A 3/2000 Axelgaard
6,041,252 A 3/2000 Walker et al.
6,041,253 A 3/2000 Kost et al.
6,048,545 A 4/2000 Keller et al.
6,057,374 A 5/2000 Huntington et al.
6,101,411 A 8/2000 Newsome
6,167,302 A 12/2000 Millot

OTHER PUBLICATIONS

"Iontophoretic Application of Drugs," Waud, J. Appl. Physiol. 23(1), 1967, pp. 128–130.

"Antibiotic Iontophoresis in the Treatment of Ear Chondritis," LaForest et al., Physical Therapy, vol. 58, No. 1, Jan. 1978, pp. 32–34.

"The Quantity and Distribution of Radiolabeled Dexamethasone Delivered to Tissue by Iontophoresis," Glass et al.; International Journal of Dermatololgy, vol. 19, Nov. 1980, 519–525.

"Iontophoretic Application of Antiviral Chemotherapeutic Agents," Hill et al., Annals New York Academy of Sciences, pp. 604–612.

"Ocular Iontophoresis," Hill et al. Paper, Louisiana State University Medical Center, School of Medicine, New Orleans, Louisiana, pp. 331–354.

"Iontophoretic Application of Adenine Arabinoside Monophosphate to Herpes Simplex Virus Type 1–Infected Hairless Mouse Skin," Park et al.; Antimicrobial Agentsand Chemotherapy, vol. 14, No. 4, Oct.; 1978, pp. 605–608.

"Iontophoresis: Applications in Transdermal Medication Delivery," Costello et al.; Physical Therapy, vol. 75, No. 6, pp. 104/554–113/563, Jun. 1995.

Physical Enhancement of Dermatologic Drug Delivery: Iontophoresis and Phonophoresis,: Kassan et al.; Journal of the American Academy of Dermatology, Apr. 1996, pp. 657–666.

"Iontophoresis and Herpes Labialis," Boxhall et al.; The Medical Journal of Australia, May 26, 1984, pp. 686–687.

"A Method of Antibiotic Administration in the Burn Patient," Rapperport et al.; Plastic and Reconstructive Surgery, vol. 36, No. 5, pp. 547–552.
"Iontophoresis for Enhancing Penetration of Dermatologic and Antiviral Drugs," Gangarosa et al., Journal of Dermatology, vol. 22, No. 11, pp. 865–875, Nov. 1995.
"Iontophoretic Treatment of Herpetic Whitlow," Gangarosa et al., Arch. Phys. Med. Rehabil., vol. 70, Apr. 1989.
"Iontophoretic Application of Antiviral Drugs," Gangarosa et al., Proceedings of an International Symposium held in Tokushima City, Japan, pp. 200–204, Jul. 27–30, 1981.
"Iontophoretic Application of Adenine Arabinoside Monophosphate for the Treatment of Herpes Simplex Virus Type 2 Skin Infections in Hairless Mice," Gangarosa, The Journal of Infectious Diseases, vol. 140, No. 6, pp. 1014, Dec. 1979.
"Effect of Iontophoretic and Topical Application of Antiviral Agents in Treatment of Experimental HSV–1 Keratitis in Rabbits," Kwon et al., Investigative Ophthalmology & Visual Science, vol. 18, No. 9, pp. 984–988, Sep., 1979.
"Acyclovir and Vidarabine Monophosphate: Comparison of Iontophoretic and Intravenous Administration for the Treatment of HSV–1 Stromal Keratitis," Hill et al., The American Journal of Medicine, Acyclovir Symposium, pp. 300–304.
"Thymine Arabinoside (Ara–T) Topical and Iontophoretic Applications for Herpes Simplex Virus Type 1 and Type 2 Skin Infections in Hairless Mice," Hill et al., Meth. And Find. Exptl. Clin. Pharmacol. 6(1), pp. 17–20, 1984.
"Iontophoresis Enhances the Transport of Acyclovir Through Nude Mouse Skin by Electrorepulsion and Electroosmosis," Volpato et al., Pharmaceutical Research, vol. 12, No. 11, pp. 1623–1627, 1995.
"Early Application of Topical 15% Idoxuridine n Dimethyl Sulfoxide Shortens the Course of Herpes Simplex Labialis: A Multicenter Placebo–Controlled Trial," Spruance et al., The Journal of Infectious Diseases, 1990; vol. 161; pp. 191–197.
"Iontophoresis for Surface Local Anesthesia," Gangarosa, JADA, vol. 88, pp. 125–128, Jan. 1974.
"Conductivity of Drugs Used for Iontophoresis," Gangarosa et al., Journal of Phamaceutical Sciences, vol. 67, No. 10, pp. 1439–1434, Oct., 1978.
"A Pilot Study of Iontophoretic Cisplatin Chemotherapy of Basal and Squamous Cell Carcinomas of the Skin," Chang et al., Arch. Dermatol., vol. 129, pp. 425–427, Apr. 1993.
"How Modern Iontophoresis Can Improve Your Practice," Gangarosa et al.; Oral Surgery, No. 10, Report 2135, Oct. 1982, pp. 1027–1038.
"Postherpetic Neuralgia," Baron et al.; Brain (1993), 116, pp. 1477–1496.
"Iontophoretic Assistance of 5–Iodo–2'–Deoxyuridine Penetration into Neonatal Mouse Skin and Effects of DNA Synthesis," Gangarosa et al., Society for Experimental Biology and Medicine, pp. 439–443, 1977.
"Electrophoretic Evaluation of the Mobility of Drugs Suitable for Iontophoresis," Kamath et al., Meth. Find., Exp. Clin. Phamacol., 1995, 17(4): pp. 227–232.
"Passive versus Electrotransport–Facilitated Transdermal Absorption of Ketorolac," Park et al.; Clinical Pharmacology & Therapeutics, vol. 63, No. 3, pp. 303–315.
"Transdermal Drug Delivery by Passive Diffusion and Iontophoresis: A Review," Singh et al.; Medicinal Research Reviews, vol. 13, No. 5, 1993, pp. 570–621.
"Iontophoresis: Electrorepulsion and Electroosmosis," Guy et al., Journal of Controlled Release 64 (2000) 129–132.
"Treatment of Common Cutaneous Herpes Simplex Virus Infections," Emmert, American Family Physician, vol. 61, No. 6, Mar. 15, 2000, pp. 1697–1704.
"Gelatin–stabilised Microemulsion–Based Oranogels: Rheology and Application in Iontophoretic Transdermal Drug Delivery," Kantaria et al., Journal of Controlled Release 60 (1999) 355–365.
"Electrotepulsion Versus Electroosmosis: Effect of pH on the Iontophoretic Flux of 5–Fluorouracil," Merino at al., Pharmaceutical Research, vol. 16, No. 6 (1999).
"Azelaic Acid: Potential as a General Antitumoural Agent," Breathnach, Medical Hypotheses (1999) 52(3) 221–226.
"Treatment of Mucocutaneous Herpes Simplex Virus Infections Unresponsive to Acyclovir with Topical Foscarnet Cream in AIDS Patients: A Phase I/II Study," Javaly et al., Journal of Acquired Immune Deficiency Syndromes 21:301–306.
"Efficacy and Safety of Azelaic Acid and Glycolic Acid Combination Therapy Compared with Tretinoin Therapy for Acne," Spellman et al., Clinical Therapeutics, vol. 20, No. 4, 1998.
"Passive Versis Electrotransport–Facilitated Transdermal Absorption of Ketorolac," Park et al., Clinical Pharmacology & Therapeutics, vol. 63, No. 3, pp. 303–315.
"Soriudine Versus Acyclovir for Treatment of Dermatomal Herpes Zoster in Human Immunodeficiency Virus–Infected Patients: Results from a Randomized, Controlled Clinical Trial," Gnann et al., Antimicrobial Agents and Chemotherapy, vol. 42, No. 5, May 1998, pp. 1139–1145.
"Azelaic Acid 20% Cream (AZELEX®) and the Medical Management of Acne Vulgaris," Gibson, Dermatology Nursing, vol. 9, No. 5, pp. 339–344.
"Sorivudine: A Promising Drug for the Treatment of Varicella–Zoster Virus Infection," Whitley, Neurology 1995; 45 (Supp. 8), pp. S73–S75.
"Transdermal Drug Delivery by Passive Diffusion and Iontophoresis: A Review," Singh et al., Medicinal Research Reviews, vol. 13, No. 5, pp. 569–61 (1993).
"Antiherpesviral and Anticellular Effects of 1–β–D–Arabinofuranosy–E–5–(2–Halogenovinyl) Uracils," Machinda et al., Antimicrobial Agents and Chemotherapy, Jul. 1981, pp. 47–52.
"Herpes Simplex," American Academy of Dermatology.
"Common Cold" Virus is Near, Haney, The Associated Press, Jan. 15, 2000.
"New Medicines Move to Eradicate Acne," Hemphill, The New York Times, Feb. 29, 2000.
"Warts," American Academy of Dermatology, American Academy of Dermatology, 1997, Revised 1991, 1993.
"Psoriasis," American Academy of Dermatology, 1994.
"Eczema/Atopic Dermatitis," American Academy of Dermatology, 1987, Revised 1991, 1993, 1995.
"Skin Cancer: An Undeclared Epidemic," American Academy of Dermatology, 1988, Revised 1989, 1993, 1994.
File History of U.S. Pat. No. 5,676,648 to Henley.
File History of U.S. Pat. No. 5,879,323 to Henley.

METHODS FOR IONTOPHORETIC DELIVERY OF ANTIVIRAL AGENTS

Matter enclosed in heavy brackets [ ] appears in the original patent but forms no part of this reissue specification; matter printed in italics indicates the additions made by reissue.

[REFERENCE TO RELATED APPLICATIONS

This application is a continuation-in-part of application Ser. No. 08/868,499 filed Jun. 4, 1997, now U.S. Pat. No. 5,879,323 issued Mar. 9, 1999, which is a divisional of allowed U.S. patent application Ser. No. 08/646,853 filed May 8, 1996 now U.S. Pat. No. 5,767,648.]

BACKGROUND OF THE INVENTION

1. Field of the Invention

This invention relates generally to the transdermal electrokinetic mass transfer of medication into a diseased tissue, and, more specifically, to a portable apparatus for the iontophoretic delivery of medication across the skin and incorporation of the medication into diseased tissues and blood vessels adjacent to the delivery site. The apparatus provides a new method for treating and managing diseases presenting cutanoeus lesions.

2. Prior Art

Iontophoresis has been employed for several centuries as a means for applying medication locally through a patient's skin and for delivering medicaments to the eyes and ears. The application of an electric field to the skin is known to greatly enhance the skin's permeability to various ionic agents. The use of iontophoretic transdermal delivery techniques has obviated the need for hypodermic injection for many medicaments, thereby eliminating the concomitant problems of trauma, pain and risk of infection to the patient.

Iontophoresis involves the application of an electromotive force to drive or repel oppositely charged ions through the dermal layers into a target tissue. Particularly suitable target tissue include tissues adjacent to the delivery site for localized treatment or tissues remote therefrom in which case the medicament enters into the circulatory system and is transported to a tissue by the blood. Positively charged ions are driven into the skin at an anode while negatively charged ions are driven into the skin at a cathode. Studies have shown increased skin penetration of drugs at anodic or cathodic electrodes regardless of the predominant molecular ionic charge on the drug. This effect is medicated by polarization and osmotic effects.

Regardless of the charge of the medicament to be administered, a iontophoretic delivery device employs two electrodes (an anode and a cathode) in conjunction with the patient's skin to form a closed circuit between one of the electrodes (referred to herein alternatively as a "working" or "application" or "applicator" electrode) which is positioned at the delivered site of drug delivery and a passive or "grounding" electrode affixed to a second site on the skin to enhance the rate of penetration of the medicament into the skin adjacent to the applicator electrode.

Recent interest in the use of iontophoresis for delivering drugs through a patient's skin to a desired treatment site has stimulated a redesign of many of such drugs with concomitant increased efficacy of the drugs when delivered transdermally. As iontophoretic delivery of medicaments become more widely used, the opportunity for a consumer/patient to iontophoretically administer a transdermal dosage of medicaments simply and safely at non-medical or non-professional facilities would be desirable and practical. Similarly, when a consumer/patient travels, it would be desirable to have a personal, easily transportable apparatus available which is operable for the iontophoretic transdermal delivery of a medication packaged in a single dosage applicator. The present invention provides a portable iontophoretic medicament delivery apparatus and a unit-dosage medicament-containing applicator electrode which is disposable and adapted for use with the apparatus for self-administering medicament.

SUMMARY OF THE INVENTION

The present invention discloses a portable iontophoretic transdermal or transmucoscal medicament delivery apparatus and a unit dosage medicament applicator electrode adapted for use with the apparatus for the self-administration of a unit dose of a medicament into the skin. The apparatus is particularly suited for the localized treatment of herpes infections. Recurrent herpetic infections (fever blisters or herpes labialis) are very common and usually involve the mucocutaneous juncture. The established treatment for recurrent herpetic lesions (oral or genital) has been primarily supportive; including local topical application of anesthesia. Severe cases have been treated with systemic Acyclovir® (Zovirax Burroughs-Wellcome). Some cases the condition is managed with prophylactic long-term dosing administration with a suitable antiviral agent at great expense. Systemic treatment of acute herpetic flare-ups may reduce the normal 10–12 day course of cutaneous symptoms into a 6–8 day episode. Topical treatment of lesions with Acyclovir® has not been as effective as in vitro studies would suggest. A compound which is not presently available to clinicians but has demonstrated significant anti herpetic activity is 5-iodo-2 deoxyuridine (IUDR). Both of those agents have shown limited clinical efficacy when applied topically to the herpetic lesion. It is the present inventor's contention that the limited efficacy of topical administration previously observed is, at least in part, due to the poor skin penetration of these medicaments when applied topically. The present invention provides improved transdermal delivery of these medicaments and demonstrates improved clinical results in the case of Herpes.

Oral Herpes (most commonly Herpes simplex I infection) as well as genital Herpes (usually Herpes Simplex II infection) afflict many people, cause discomfort, shame, and may contribute to more severe and costly illnesses such as cervical cancer, prostate cancer, and perinatal blindness from herpetic conjunctivitis. The present invention discloses a portable, user-friendly transdermal delivery device and a method for using the device with Acyclovir® (or similar antiviral agent) to greatly benefit these afflicted patients. The present inventor has constructed embodiments of this device and conducted human clinical trials which clearly demonstrate improved therapeutic efficacy using iontophoretically administered antiviral agents when compared to unassisted topical application of the agent.

It is an object of the present invention to provide an iontophoretic medicament delivery apparatus which is portable and operable for self-administration of medicament into the skin of a person.

It is another object of the present invention to provide an improved iontophoretic transdermal drug delivery apparatus having a medicament-containing application electrode which disperses a single dosage and is disposable and non-reusable.

It is a feature of the present invention that the iontophoretic medicament delivery apparatus is easily maneuverable and operable when hand-held.

It is another feature of the present invention that the iontophoretic medicament delivery apparatus is battery powered and conveniently transported by a person.

It is a further feature of the present invention that the iontophoretic medicament delivery apparatus employs a tactile electrode which is in electrical contact with the skin of a user's hand when the apparatus is held in the user's hand, obviating the need for a separate grounding electrode connector or wire.

It is still another feature of the present invention that the iontophoretic medicament delivery apparatus is adapted to be operable with a disposable medicament containing applicator electrode which applicator electrode includes an absorbent, inert, non-corrosive portion containing a therapeutic agent.

It is yet another feature of the present invention to provide an embodiment of an iontophoretic transdermal delivery device wherein the disposable iontophoretic medicament-containing applicator electrode is adapted for releasable attachment to use with a hand-held base assembly housing a grounding electrode.

It is yet another feature of the present invention that the disposable iontophoretic medicament applicator electrode include indicator means operable for enabling a user to determine when the medicament within the removable applicator electrode has been released in delivery and/or depleted.

It is yet another feature of the present invention that the circuitry employed in the disposable iontophoretic medicament applicator include current limiting means operable for limiting the electrical current flowing between the surface of the applicator and the skin to less than about one milliampere per square centimeters of application electrode skin-contacting, surface.

It is another advantage of the present invention that the iontophoretic medicament delivery apparatus employs a disposable application electrode which conducts the electrical current to the tissue through the solution in which the medicament is dissolved.

It is still another advantage of the present invention that the improved disposable iontophoretic medicament applicator is inexpensive, safe to use, substantially unitary in construction and greatly increases the therapeutic efficacy of a medicament administered thereby.

The apparatus in accordance with the present invention provides a means for topically administering medicament directly and with, high efficiency into a diseased tissue thereby providing a novel method for treating clinical conditions presenting mucocutaneous symptoms and particularly mucocutaneous Herpes Simplex viral eruptions and sequelle associated therewith.

In one embodiment the electrode comprises a unitary flexible strip (such as SILASTIC®- by Dow Corning) having perforations dimensioned to accommodate a medicament placed therein. The perforations or "cells" can be made to store and dispense gels, ointments, fluids and other medicament vehicles without requiring the reformulation of the either the medicament or the vehicle.

The above objects, features and advantages of the invention are realized by the improved monopolar iontophoretic, medicament applicator which is easily transportable. The applicator employs a detachable medicament containing application electrode. The objects, features and advantages of the invention will become apparent upon consideration of the following detailed disclosure of the invention, especially when it is taken in conjunction with the accompanying drawings wherein:

DESCRIPTION OF THE PREFERRED EMBODIMENT

Figure 1:
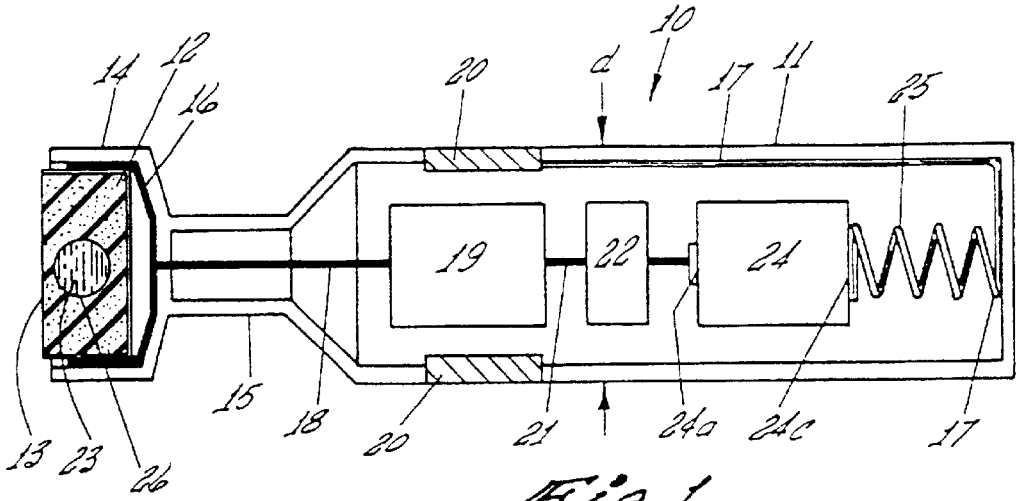
FIG. 1 is a side elevational plan view of the iontophoretic medicament delivery apparatus showing the circumferential tactile ground electrode on the outer surface of the base housing and a disposable iontophoretic application electrode.

FIG. 1 shows, in side elevation, a preferred embodiment of the hand-held iontophoretic transdermal medicament delivery apparatus of the present invention. The apparatus, indicated generally by the numeral 10, has an elongate base assembly 11 the major portion of which is preferably formed of plastic and shaped to conform to and comfortably fit with a user hand. An applicator electrode module 12, containing a unit dose of medicament 23, is releasably attached to a applicator electrode receptacle 14 on the distal end of the base assembly 11. The application electrode 12 is preferably a "clip-on" type of electrode similar in configuration to an electrocardiogram electrode. In the drawing presented in FIGS. 1 and 2, electrically conductive elements such as wires and busses are presented as heavy lines. A wire 16 provides electrical connection between the applicator electrode receptacle 14 and wire 1 within the neck 15 of the base assembly 11. Connecting wire 18, in turn, provides electrical connection between the wire 16 and the current driver unit 19 housed within the base assembly 11. A conductive tactile electrode 20 forms a portion of the exterior skin-contacting surface of the base assembly 11 preferably circumferentially enclosing a portion of the base housing or it may be interrupted or discontinuous on the outer surface. The tactile electrode 20 is in electrical communication with the cathode 24C of battery 24 by means of a buss 17 and conductive urging spring 25 which secures the battery in position within the base assembly 11. For the self-administration of medicament a user must have, skin contact with the tactile electrode 20 for the unit to operate. Current driver 19 underlies the cathodic (ground) tactile electrode 20 and is electrically connected via wire 21 to a voltage multiplier 22. The voltage multiplier 22 receives low voltage power from the anode 24a of the battery power source 24 and increases the available voltage for presentation to the application electrode 12. The battery 24 is preferably a size AA or AAA. Battery 24 is held in place by an electrically conductive biasing spring 25 and ensures that electrical power is available at the application electrode 12 when the user grasps and holds the base housing 11 of the apparatus 10 thereby touching the cathodic tactile electrode 20. The application electrode 12 and the tactile electrode 20 thus form a closed circuit in series with the user's skin.

When current flows across the user's skin to the application electrode in response to an applied voltage the current promotes and hastens the penetration of the medicament 23 contained in a reservoir 26 within the working electrode 12 into the skin. The polarity of the working electrode 12 is preferably unidirectional to promote the above described penetration without requiring a separate grounding electrode. The working application electrode 12 will be described in greater detail below.

The base assembly 11 of apparatus 10 serves as a housing to the aforesaid components as a handle. The portion of the base assembly 11 exclusive of the tactile electrode, is preferably made of a plastic such as polyethylene, acrylonitrile, butadiene, styrene or similar durable plastic. The battery portion 24 is connected to a voltage multiplier 22 which steps up the voltage supplied by the battery 24 and applies the stepped up voltage to the current driver 19. Current driver 19 presents a defined current and voltage output at the application electrode 12 the value of the current, which may be empirically determined being sufficient to drive the medicament through the porous, open-celled material 27 (FIG. 2) within the application electrode interposed between the skin contacting surface 13 and reservoir 26 containing the unit dose medicament and penetrate the patient's skin. The circuitry limits the maximum current available to the application electrode to preferably to less than about one milliampere per two square centimeters of the skin-contacting surface area 13 of the application electrode 12. However, depending upon working electrode's 12 skin-contacting surface 13 configuration, the current level can vary from about 0.1 to about 1.2 milliamps. Currents ranging between 0.1 ma to 5 ma have been used clinically by the present inventor, but the higher currents caused the user minor discomfort and, with chronic use over time, may produce untoward effects.

Figure 2:
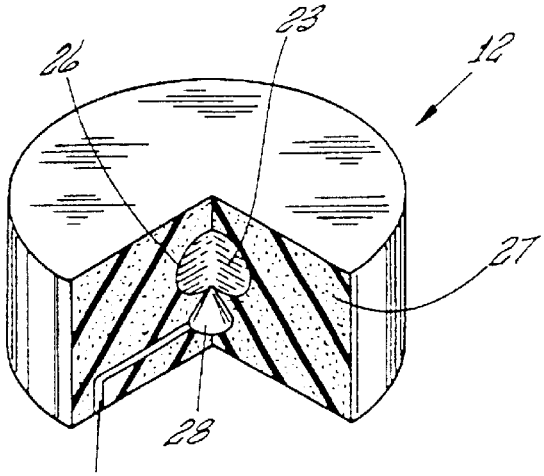
FIG. 2 is a side elevational view of the disposable non-reusable iontophoretic application electrode with a portion broken away to view the medicament dose packet.

FIG. 2 shows a preferred embodiment of the iontophoretic medicament-containing application electrode 12. The application electrode 12 is preferably disposable and non-reusable and is suitable, for example, for transdermally delivering antiviral agents such as Acyclovir® for the treatment of cold sores or genital herpes. The size of the skin-contacting surface 13 or application electrode 12 may vary to accommodate specific clinical applications. The application electrode 12 is detachably housed within a recess within the receptacle 14 which recess presents an electrically conductive interior surface to complete the electrical flow path from the connecting wires 18 and 16 to a conductive element 29 within the application electrode. The electrical current from the current driver 19 is conducted through conductive inner surface of the application electrode receptacle 14 to the electrically conductive element 29 within the applicator electrode which element 29 is in electrical contact with the inner surface of the receptacle in contact therewith to drive the medicament 23 or treatment agent through the open-celled sponge-like matrix material 27 and through the user's skin (not shown). The medicament or treatment agent 23 is contained within a rupturable polymer reservoir 26 until dispensed during treatment. A slight exertion of pressure or squeezing of the reservoir 26 against reservoir puncture means 28 releases the medicament or treatment agent into an open-celled sponge-like material 27 within the application electrode for iontophoretic delivery into the patient's skin. Medicament 23 release can occur at the time of application or upon peruse compression of the electrode 12. Application electrode 12 can be advantageously designed to include a stripping portion adapted to that upon removal of the application electrode 12 from the electrode receptacle 14 a protruding stripping portion (not shown) scrapingly strips the conductive coating from the conductive support arm 29 to prevent reuse of the disposable electrode 12. Application electrode 12 in intentionally packaged with a single dose packet or reservoir 26 of treatment agent or medicament 23. In addition to the medicament, the reservoir 26 can include a coloring agent, such as iodine, which turns dark blue upon contact with starch in the open-celled material to visibly indicate that the unit dose encapsulation has been used. Other suitable coloring agents can include pH indicators, wet saturation indicators or oxidizable pigments.

The open-celled sponge-like material 27 surrounding reservoir 26 should be inert to the medicament or treatment agent being employed, as well as being non-corrosive and stable when in contact with the treatment agent. Suitable materials include plastic pads, such as polyethylene, paper or cotton, porous ceramics, open-celled porous polytetrafluoroethylene, polyuethane and other inert plastics, and open-celled silicone rubber, such as may be employed with vertically aligned medicament-containing tubes. A typical medicament that can be contained within the rupturable polymer reservoir 26 is xylocaine or similar topical anesthetic.

The disposable electrode 12 possesses the advantages of preventing leaching or migration of the medicament from within the rupturable polymer reservoir, no attendant loss of efficacy, a long shelf life and little or no electrode corrosion. A suitable electrical control circuit for use in the iontophoretic medicament delivery apparatus 12 is shown in U.S. patent application Ser. No. 07/579,799, filed Sep. 10, 1990, now U.S. Pat. No. 5,160,316 and hereby specifically incorporated by reference herein in pertinent part.

Figure 3:
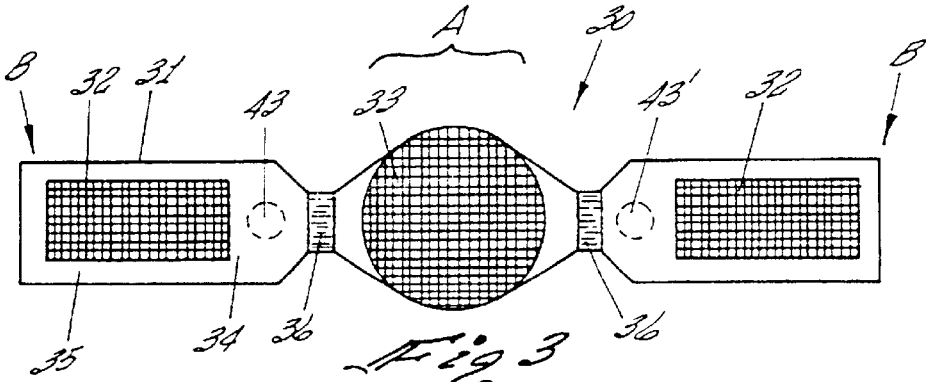
FIG. 3 is a top view of a medicament dispensing electrode adapted for use with an iontophoresis handpiece.

FIG. 3 shows a particularly preferred embodiment of a disposable, one-time use electrode 30 for use with the iontophoresis handpiece 10 of the present invention. FIG. 3 is a top view of the disposable electrode 30 with the upper release film 41 (FIG. 4) removed. A non-conductive substrate 31 is formed into a flat strip having a central portion A and two end portions B. The end portions B each have a cut-out therein containing an electrically conductive gel 32. The gel 32 may be imbedded within a mesh or it may be constrained within the cut out by means of a porous, non-wicking and non-electrically conducing containment layer 34 and 35 much as tea is contained within a porous tea bag. The central portion A of the strip 31 has a medicament-containing reservoir 33 therewithin. The medicament-containing reservoir 33 may comprise a suitable medicament embedded within the mesh of a pharmacologically inert material. The medicament-containing reservoir 33 is positioned between die cuts 36 in the non-conductive substrate 31 which die cuts provide means for facilitating the predictable bending the electrode strip 30 to matingly conform to the shape of the exterior surface of an iontophoresis handpiece 10 (FIG. 1) Magnets 43 and 43' (shown in phantom in FIG. 3) disposed laterally to the central portion A provide means for magnetically activating a handpiece when the electrode is in position.

Figure 4:
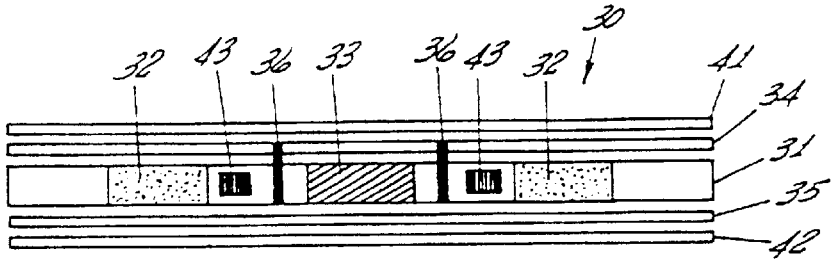
FIG. 4 is a side elevational exploded view of the medicament dispensing electrode of FIG. 3.

An exploded side view of the electrode 30 is shown in FIG. 4. The conductive gel 32 filling the cut-outs may be contained within a mesh or may be contained within the cut-out by means of porous, non-wicking layers 34 and 35. Similarly, the medicament-containing cut-out 33 may comprise the medicament embedded within a mesh, a gel, or similar substrate which releases the medicament in response to an electrical communication therewith. The upper containment layer 34 and the lower containment layer 35 serve to restrain the conductive gel within the medicament reservoir 33 to their respective cut-outs. An upper release film 41 is used to protect the adhesive surface (not shown) on the uppermost surface of the containment layer 34. A lower release film 42 serves a similar function to protect the adhesive surface of the lower medicament containment layer 35. The cut-outs 36 are shown to penetrate the strip of non-conductive material 31 adjacent to the medicament-containing reservoir 33. It is particularly desirable to provide one or more activating magnetic bodies 43 and 43' within the strip 31 in order to properly position the electrode strip 30 and activate the handpiece 10. Since it is anticipated that the handpiece/electrode assembly of the present invention will most likely be used in the bathroom, it is particularly desirable to hermetically seal the handpiece's internal operational mechanisms. The on/off switch within the handpiece can be in the form of a magnetically responsive switch which is turned "on" and "off" in response to the position of the electrode.

Figure 5:
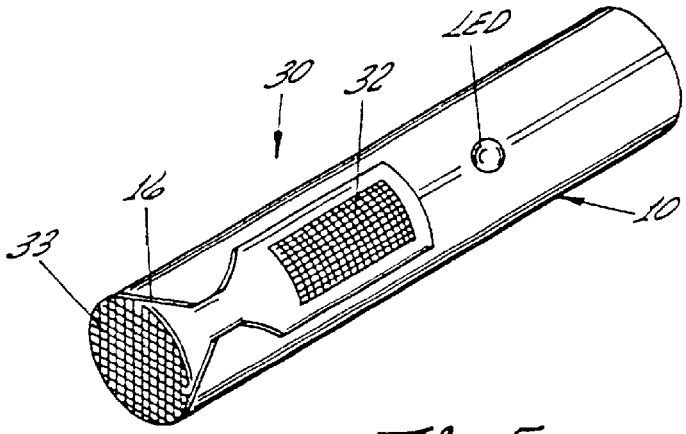
FIG. 5 is a perspective view illustrating the medicament dispensing electrode of FIG. 3 and 4 attached to an iontophoresis handpiece in preparation for use.

Turning now to FIG. 5, we see a disposable electrode 30 in the process of being applied to the terminal end of an iontophoresis handpiece 10. The electrode 30 is applied to the active terminal 16 of the handpiece in such a manner that the medicament-containing reservoir 33 overlies and is in electrical contact with the active terminal 16 of the handpiece 10. The conductive gel layers 32 are positioned on the handpiece to overly the ground electrode on the handpiece 10. The ground electrode is indicated at 20 in FIG. 5.

An alternate but equally effective embodiment of FIG. 4 electrode can be manufactured from a mold injected soft, inert material, non-conductive and non-porous (such as SILASTIC®- by Dow Corning) in the shape embodied in FIG. 3. The unit will contain vertically aligned open cells for containing and acting as reservoir for therapeutic medicaments as well as a conductive gel (if necessary). Such an embodiment is less costly to produce and avoids the process of assembling numerous layers.

Figure 6:
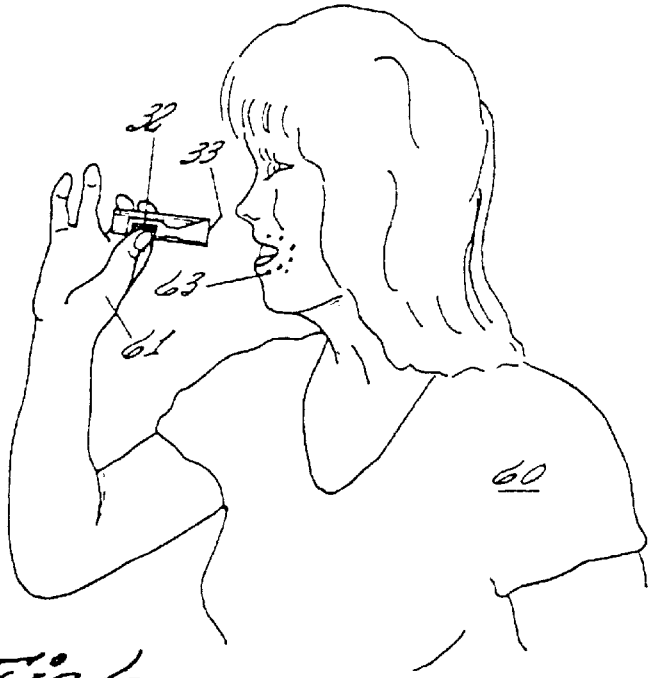
FIG. 6 is a perspective view illustrating a patient preparing to self-administer medicament to lesions adjacent to the mouth employing the iontophoretic electrode/handpiece delivery system in accordance with the present invention.

The iontophoresis handpiece and electrode assembly in accordance with the preferred embodiment shown in FIGS. 3 and 4 is shown being used by a patient 60 in FIG. 6. The patient 60 grasps the handpiece by means of placing a finger 61 on at least one of the conductive gel ground electrodes thereby grounding the patient's body. The active electrode driver 19 of the handpiece is in electrical communication with the medicament-containing reservoir 33. The medicament-containing reservoir 33, thus positioned and grasped by the patient, is advanced to come in contact with a lesion 63 on the patient's skin. Upon contact, electrical current flows between the active electrode 19 in the handpiece to the ground electrode(s) 32 via passage through the medicament-containing reservoir 33 comprising the active electrode. The polarity of the current may be reversed to accommodate the charge on the medicament. The flow of an electrical current facilitates entry of the medicament within the reservoir 33 into the skin overlying the lesion 63 thereby locally delivering the medicament to the exact area to be treated.

EXPERIMENTAL CLINICAL TRIALS

The inventor has conducted a clinical study using a prototype iontophoretic device in accordance with the present invention for the treatment of cold sores. The clinical response was promising. A second independent, qualified investigator, a board-certified Urologist, conducted a study using the present apparatus and method for treating male genital herpes lesions with encouraging results. Table 1 summarizes data (discussed below) supporting the claim to unexpected clinical benefits treating disease with this novel method. The method and medicament application device when used together for treating these common embarrassing, and previously not easily-treatable ailments provide surprising advantages.

The embodiment of the device shown in FIG. 1 and described hereinabove is a improvement over the prototype used in the clinical study, which was a larger unit, not user friendly, which required physically connecting wires to the patient's body which created anxiety, and could not be used without attending personnel. Notwithstanding design, the apparatus used in the clinical study summarized in Table 1 employed electronics similar to the apparatus described herein and was used to optimize the clinical performance of the embodiment 12 of the device described herein.

TABLE 1

STAGE TREATMENT RESULTS

| RESPONSE | IUDR | ACYCLOVIR ® | TOTALS |
|---|---|---|---|
| No response | 1 | 1 | 2 |
| Some response | 1 | 3 | 4 |
| Major response | 26 | 42 | 68 |

The study included a control situation wherein seven patients were found who had simultaneous concurrent herpes lesions at separate locations on their bodies. In each case one lesion was treated with iontophoretic application of antiviral agent (Acyclovir® of IUDR) and the other lesion was treated in the standard method employed in the prior art comprising repeated topical application of the same antiviral comprising repeated topical application of the same antiviral agent. The iontophoretically enhanced treated lesion received a single 10–15 minute treatment. All iontophoretically treated lesions demonstrated resolution in 24 hours and none of the unassisted topically treated lesions demonstrated a similar response. The results for the control group are summarized in Table 2.

TABLE 2

CONTROL GROUP RESULTS

| | No response | Some resp. | Major resp. |
|---|---|---|---|
| IUDR | | | |
| Treated lesion | 0 | 0 | 7 |
| Control lesion | 5 | 2 | 0 |
| ACYCLOVIR ® | | | |
| Treated lesion | 0 | 0 | 1 |
| Control lesion | 1 | 0 | 0 |

The clinical studies included patient volunteers with fill informed consent who suffered from recurrent cold sores. The study demonstrated greatest treatment efficacy if the herpes lesion received iontophoretic treatment within 36 hours of lesion onset. The treatment incorporated an electrode saturated with Acyclovir® ointment (ZOVIRAX®) or IUDR (STOXIL®) Ophthalmic drops as supplied by the manufacturer. Thus mounted Anodic electrode of the prototype system was used for a 10–15 minute application directly to the lesion with the average current setting of 0.2 ma–0.6 ma which was well tolerated by all patients.

The lesion was evaluated in 24 hours. In 92% of the iontophoretically treated cases (>70 lesions treated) a major response was noted. A major response was categorized by resolution of pain in >6 hours and lesion crusted and healing within 24 hours. The normal course of cold sores involves an average period of 10–12 days before resolution and healing occurs. The present apparatus and clinical method for treatment of mucocutaneous Herpes Simplex (type I and Type II) eruptions presented herein have been described and performed with excellent results. This novel user friendly apparatus in combination with the disclosed clinical treatment method presents a very effective new treatment for Herpes Simplex eruptions.

While the invention has been described above with references to specific embodiments thereof, it is apparent that many changes, modifications and variations in the materials, arrangements of parts and steps can be made without departing from the inventive concept disclosed herein. For example an impregnated conductive gel can also be used to as medicament containing medium to increase the physical stability and the tissue adhering characteristics of the electrode. Accordingly, the spirit and broad scope of the appended claims is intended to embrace all such changes, modifications and variations that may occur to one of skill in the art upon a reading of the disclosure. All patent applications, patents and other publication cited herein are incorporated by reference in their entirety.

What I claim is:

1. A disposable medicament dispensing applicator electrode [for] *and* an iontophoretic [drug] *medicament* delivery device adapted for the self-administration of a medicament into a person's skin *at a localized treatment site,* said device comprising a base assembly having an active terminal adapted to receive and make electrical contact with [a detachable] *said* medicament dispensing applicator electrode, [wherein said base assembly comprises:] a case having an elongate, substantially cylindrical outer surface having a size and shape adapted to be comfortably grasped within a person's hand, [and wherein] at least a portion of said outer surface [is a] *including* tactile electrode formed of an electrically conductive material[;], and a bipolar electrical power means having a first pole and a second pole[;], said electrical power means being enclosed within said case and [wherein] said first pole [is] *being* in electrical communication with said tactile electrode; [wherein] said medicament dispensing applicator electrode [comprises:] *including* a module containing a unit dose of medicament[, an electrically conductive working electrode] and means thereon adapted for releasably attaching said applicator electrode to said *device in electrical contact with said* second pole of said electrical power means, [wherein] said applicator electrode further [comprises] *comprising* an elongate strip constructed of a substantially electrically non-conductive substrate material, said strip having a central portion containing [a] *the* medicament [in an electrically conductive substrate] *for iontophoretic delivery of the medicament into the person's skin at the treatment site upon completion of an electrical circuit from said power means through said active terminal and said tactile electrode via the person's skin at the treatment site,* and said strip having laterally symmetric end portions having cutouts therewithin.

2. The disposable medicament dispensing applicator electrode of claim 1 wherein said cutouts in said laterally symmetric end portions contain an electrically conductive material.

3. The disposable medicament dispensing applicator electrode of claim 2 wherein said electrically conductive material is a gel.

[4. A disposable medicament dispensing applicator electrode for an iontophoretic drug delivery device adapted for the self-administration of a medicament into a person's skin, said device comprising a base assembly having an active terminal adapted to receive and make electrical contact with a detachable medicament dispensing applicator electrode wherein said base assembly comprises; a case having an elongate, substantially cylindrical outer surface having a size and shape adapted to be comfortably grasped within a person's hand and wherein at least a portion of said outer surface is a tactile electrode formed of an electrically conductive material; and a bipolar electrical power means having a first pole and a second pole; said electrical power means being enclosed within said case and wherein said first pole is in electrical communication with said tactile electrode; wherein said medicament dispensing applicator electrode comprises: a module containing a unit dose of medicament, an electrically conductive working electrode and means thereon adapted for releasably attaching applicator working electrode to said second pole of said electrical power means wherein said applicator electrode further comprises an elongate strip constructed of a substantially electrically non-conductive substrate material, said strip having a central portion containing a medicament in an electrically conductive substrate and said strip having laterally symmetric end portions having cutouts therewithin.]

*5. A combination disposable medicament dispensing applicator electrode and drug delivery device for electrokinetic self-administration of a medicament into an individual's skin at a localized treatment site, said device including a base assembly having an active terminal for receiving and making electrical contact with the medicament dispensing applicator electrode, said base assembly comprising a case including an outer surface having a size and shape for comfortably grasping within an individual's hand, a portion of said outer surface including a tactile electrode formed of an electrically conductive material and a bipolar electrical power means having a first pole and a second pole, said electrical power means being enclosed within said case, said first pole being in electrical contact with said tactile electrode, said medicament dispensing applicator electrode comprising an elongated strip containing a medicament, and means for releasably attaching said applicator electrode to said case in electrical contact with said second pole of said electrical power means, said strip being formed of a substantially electrically non-conductive strip material having a portion thereof containing a medicament, said device and said electrode being operable to electrokinetically effect delivery of the medicament in said strip to the individual's skin at the treatment site in contact with said substrate in response to completion of an electrical circuit between said second pole through said strip and via the individual's contacted skin at the treatment site and said first pole through said tactile electrode when the device is grasped by the individual.*

*6. A combination according to claim 5 wherein the medicament is charged.*

*7. A combination according to claim 5 wherein said non-conductive strip material portion contains a conductive gel to facilitate electrokinetic delivery of the medicament into the individual's skin at the treatment site.*

* * * * *